United States Patent [19]

Schweich, Jr. et al.

[11] Patent Number: 5,716,340
[45] Date of Patent: Feb. 10, 1998

[54] BLOOD PERFUSION CATHETER

[75] Inventors: Cyril J. Schweich, Jr., St. Paul; Kent D. Harrison, Brooklyn Park; Matthew M. Burns, Orono, all of Minn.

[73] Assignee: Scimed Life Systems, Inc., Maple Grove, Minn.

[21] Appl. No.: 715,126

[22] Filed: Sep. 17, 1996

Related U.S. Application Data

[63] Continuation of Ser. No. 201,069, Feb. 24, 1994, Pat. No. 5,558,642, which is a continuation of Ser. No. 740,047, Aug. 2, 1991, abandoned.

[51] Int. Cl.⁶ .................................................. A61M 29/00
[52] U.S. Cl. .................................................. 604/101
[58] Field of Search ............... 604/96–103; 606/192–194

[56] References Cited

U.S. PATENT DOCUMENTS

| | | |
|---|---|---|
| 550,238 | 11/1895 | Allen, Jr. . |
| 2,175,726 | 10/1939 | Gebauer . |
| 2,642,874 | 1/1953 | Keeling . |
| 2,687,131 | 8/1954 | Raiche . |
| 2,854,982 | 10/1958 | Pagano . |
| 3,173,418 | 3/1965 | Baran . |
| 3,516,408 | 6/1970 | Montanti . |
| 3,888,249 | 6/1975 | Spencer . |
| 3,923,065 | 12/1975 | Nozick et al. . |
| 4,141,364 | 2/1979 | Schultze . |

(List continued on next page.)

FOREIGN PATENT DOCUMENTS

| | | |
|---|---|---|
| 0246998 | 11/1987 | European Pat. Off. . |
| 0383429A2 | 8/1990 | European Pat. Off. . |
| 0399712 | 11/1990 | European Pat. Off. . |
| 0436898A1 | 7/1991 | European Pat. Off. . |
| 3235974A1 | 6/1983 | Germany . |
| 3516830C2 | 11/1986 | Germany . |
| 3620123A1 | 12/1987 | Germany . |
| 3621350A1 | 1/1988 | Germany . |
| 984471 | 1/1983 | U.S.S.R. . |
| 1069826A | 1/1984 | U.S.S.R. . |
| WO88/00071 | 1/1988 | WIPO . |
| WO89/11307 | 11/1989 | WIPO . |
| WO89/12478 | 12/1989 | WIPO . |
| WO90/01969 | 3/1990 | WIPO . |

*Primary Examiner*—Mark Bockelman
*Attorney, Agent, or Firm*—Brinks Hofer Gilson & Lione

[57] ABSTRACT

A blood perfusion balloon catheter is provided. The perfusion catheter includes an elongate tubular shaft having a proximal portion and a distal portion and a plurality of toroidal-shaped inflatable balloons laced through the distal portion of the tubular shaft, the balloons creating a blood flow lumen when they are inflated. The perfusion catheter may also include a cylindrical sheath attached to the balloons.

10 Claims, 6 Drawing Sheets

U.S. PATENT DOCUMENTS

| | | |
|---|---|---|
| 4,183,102 | 1/1980 | Guiset . |
| 4,230,119 | 10/1980 | Blum . |
| 4,318,410 | 3/1982 | Chin . |
| 4,340,046 | 7/1982 | Cox . |
| 4,417,576 | 11/1983 | Baran . |
| 4,423,725 | 1/1984 | Baran et al. . |
| 4,437,856 | 3/1984 | Valli . |
| 4,445,892 | 5/1984 | Hussein et al. . |
| 4,447,227 | 5/1984 | Kotsanis . |
| 4,484,579 | 11/1984 | Meno et al. . |
| 4,498,473 | 2/1985 | Gereg . |
| 4,501,580 | 2/1985 | Glassman . |
| 4,512,338 | 4/1985 | Balko et al. . |
| 4,573,966 | 3/1986 | Weikl et al. . |
| 4,579,554 | 4/1986 | Glassman . |
| 4,581,017 | 4/1986 | Sahota . |
| 4,610,662 | 9/1986 | Weikl et al. . |
| 4,636,195 | 1/1987 | Wolinsky . |
| 4,641,653 | 2/1987 | Rockey . |
| 4,655,746 | 4/1987 | Daniels et al. . |
| 4,660,560 | 4/1987 | Klein . |
| 4,662,885 | 5/1987 | DiPisa, Jr. . |
| 4,681,564 | 7/1987 | Landreneau . |
| 4,696,668 | 9/1987 | Wilcox . |
| 4,705,502 | 11/1987 | Patel . |
| 4,705,517 | 11/1987 | DiPisa, Jr. . |
| 4,708,718 | 11/1987 | Daniels . |
| 4,744,366 | 5/1988 | Jang . |
| 4,762,129 | 8/1988 | Bonzel . |
| 4,763,653 | 8/1988 | Rockey . |
| 4,781,677 | 11/1988 | Wilcox . |
| 4,794,928 | 1/1989 | Kletschka . |
| 4,795,427 | 1/1989 | Helzel . |
| 4,820,298 | 4/1989 | Leveen et al. . |
| 4,824,436 | 4/1989 | Wolinsky . |
| 4,832,688 | 5/1989 | Sagae et al. . |
| 4,881,939 | 11/1989 | Newman . |
| 4,889,137 | 12/1989 | Kolobow . |
| 4,909,252 | 3/1990 | Goldberger . |
| 4,909,258 | 3/1990 | Kuntz et al. . |
| 4,923,464 | 5/1990 | DiPisa . |
| 4,927,418 | 5/1990 | Dake et al. . |
| 4,930,496 | 6/1990 | Bosley, Jr. . |
| 4,934,786 | 6/1990 | Krauter . |
| 4,950,238 | 8/1990 | Sullivan . |
| 4,976,690 | 12/1990 | Solar et al. . |
| 4,976,692 | 12/1990 | Atad . |
| 4,983,166 | 1/1991 | Yamawaki . |
| 4,983,167 | 1/1991 | Sahota . |
| 4,986,831 | 1/1991 | King et al. . |
| 4,994,033 | 2/1991 | Shockey et al. . |
| 5,000,734 | 3/1991 | Boussignac et al. . |
| 5,002,531 | 3/1991 | Bonzel . |
| 5,024,658 | 6/1991 | Kozlov et al. . |
| 5,049,132 | 9/1991 | Schaffer et al. . |
| 5,059,178 | 10/1991 | Ya . |
| 5,069,662 | 12/1991 | Bodden . |
| 5,078,685 | 1/1992 | Colliver . |
| 5,087,244 | 2/1992 | Wolinsky et al. . |
| 5,090,958 | 2/1992 | Sahota . |
| 5,090,960 | 2/1992 | Don Michael . |
| 5,092,841 | 3/1992 | Spears . |
| 5,098,381 | 3/1992 | Schneider . |
| 5,100,388 | 3/1992 | Behl et al. . |
| 5,102,402 | 4/1992 | Dror et al. . |
| 5,104,377 | 4/1992 | Levine . |
| 5,108,365 | 4/1992 | Woods . |
| 5,108,370 | 4/1992 | Walinsky . |
| 5,112,305 | 5/1992 | Barath et al. . |
| 5,129,883 | 7/1992 | Black . |
| 5,135,484 | 8/1992 | Wright . |
| 5,152,277 | 10/1992 | Honda et al. . |
| 5,160,321 | 11/1992 | Sahota . |
| 5,176,638 | 1/1993 | Don Michael . |
| 5,181,911 | 1/1993 | Shturman . |
| 5,188,595 | 2/1993 | Jacobi . |
| 5,209,717 | 5/1993 | Schmoll et al. . |
| 5,213,576 | 5/1993 | Abiuso et al. . |
| 5,213,577 | 5/1993 | Kratzer . |
| 5,226,888 | 7/1993 | Arney . |
| 5,236,413 | 8/1993 | Feiring . |
| 5,242,397 | 9/1993 | Barath et al. . |
| 5,256,141 | 10/1993 | Gencheff et al. . |
| 5,286,254 | 2/1994 | Shapland et al. . |

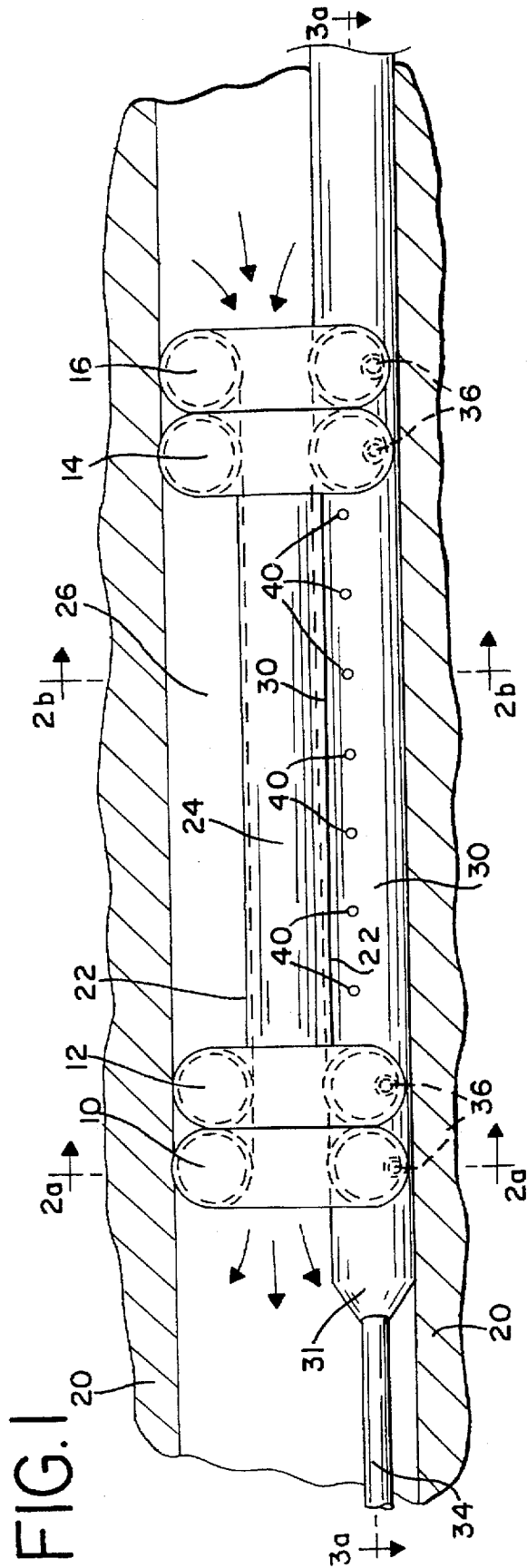

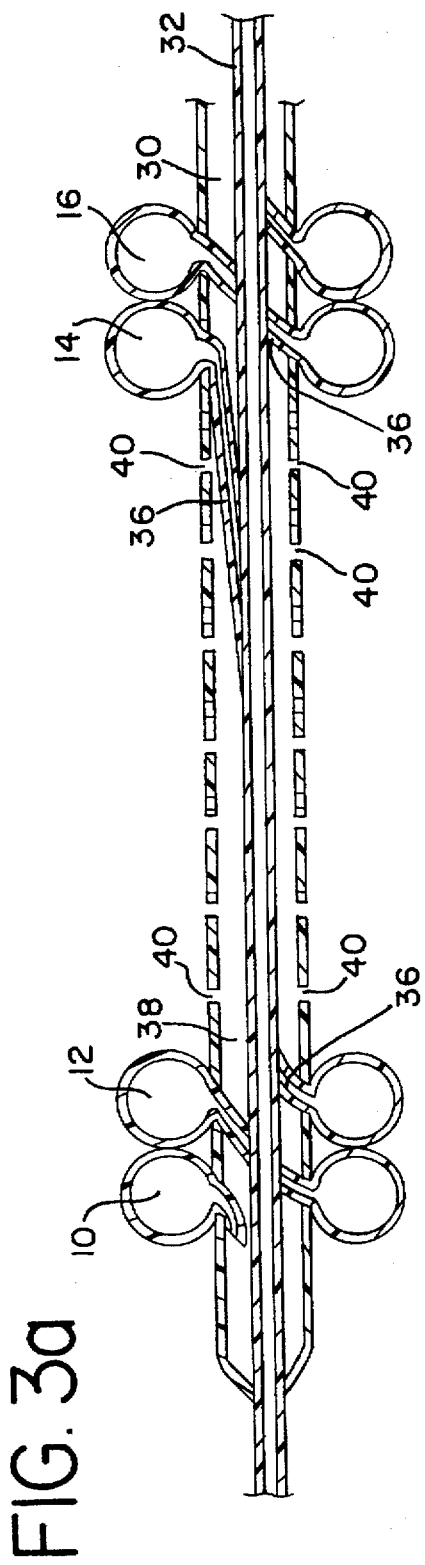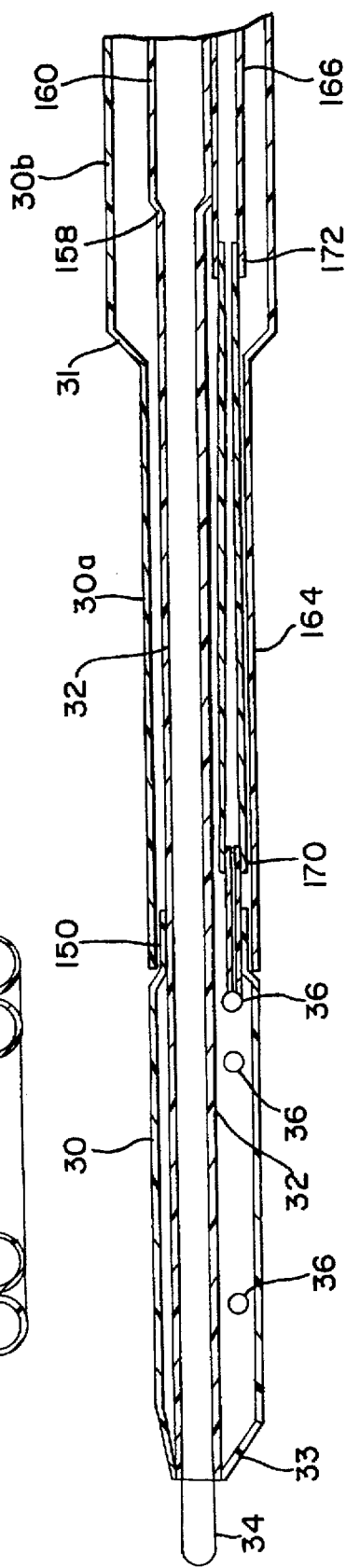
FIG. 3a
FIG. 3b

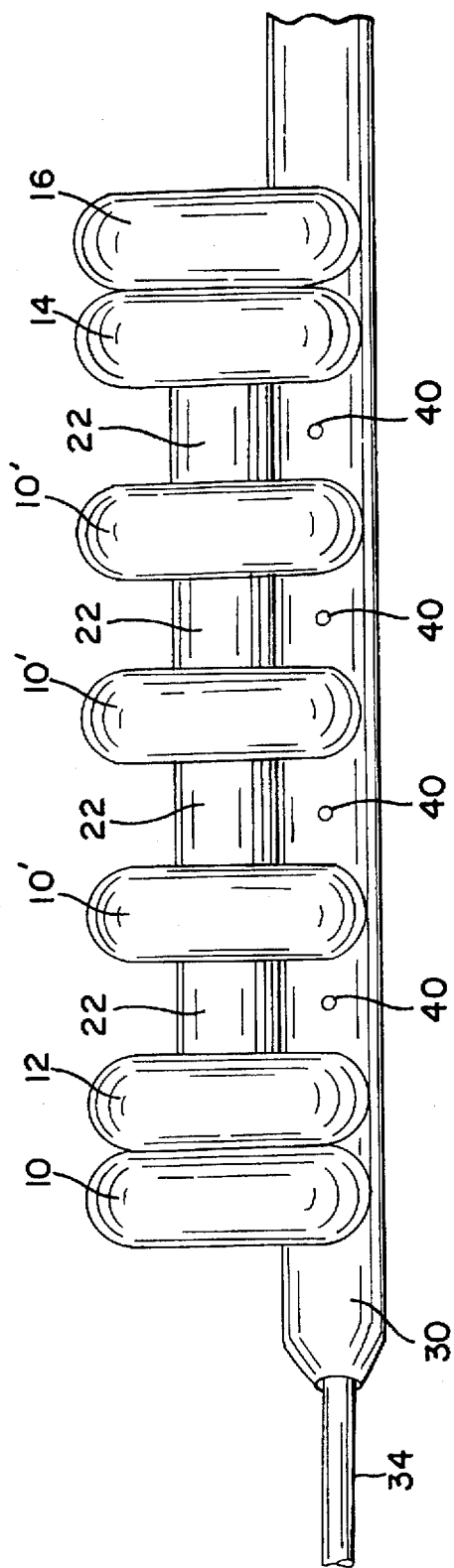
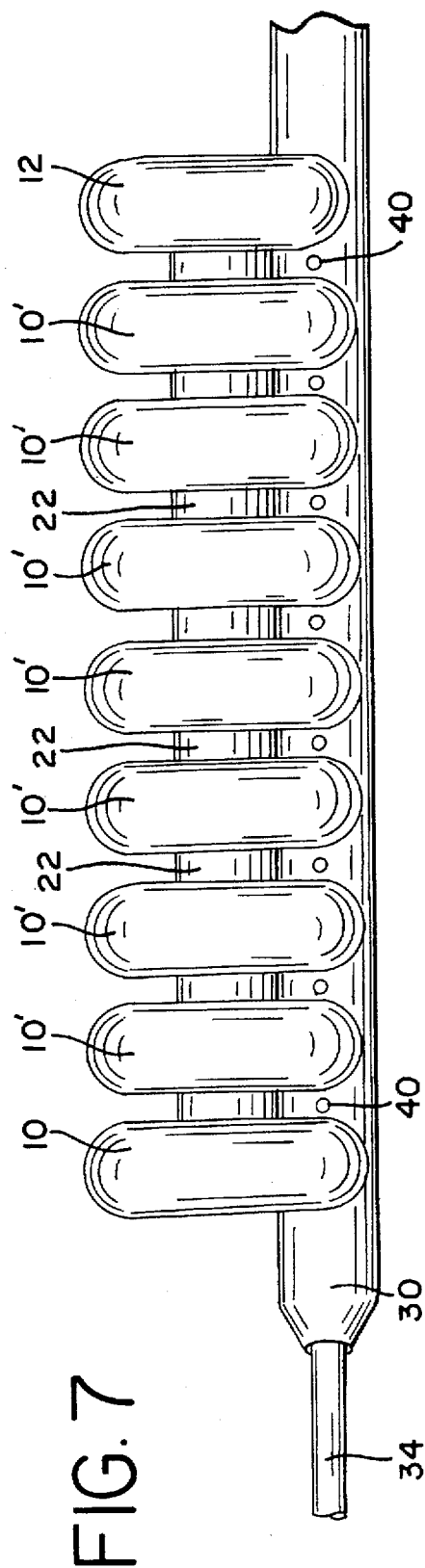
FIG. 6
FIG. 7

BLOOD PERFUSION CATHETER

This application is a continuation of application Ser. No. 08/201,069, now U.S. Pat. No. 5,558,642 filed Feb. 24, 1994 which is a file wrapper continuation of application Ser. No. 07/740,047 filed Aug. 2, 1991, now abandoned.

BACKGROUND OF THE INVENTION

The present invention relates to a drug delivery device and method. More particularly, the present invention relates to a drug delivery device and method that is flexible as to the drug agent employed and the duration of drug administration with an emphasis on physician control over deployment of both the drug and the device.

Obstructive atherosclerotic disease is a serious health problem facing our society today. This disease is the result of the deposit of fatty substances on the interior of the walls of the arteries. The build-up or accumulation of such deposits results in a narrowing of the inside diameter of the artery which in turn restricts the blood flow through the artery. This disease, wherein the opening or lumen of the artery is narrowed, is known as atherosclerosis and the accumulation is known as a lesion.

One commonly used procedure for treating an obstruction caused by atherosclerosis is a procedure known as coronary artery bypass graft surgery ("bypass surgery"). Although bypass surgery has been used with moderate success in the treatment of atherosclerosis, it can be extremely invasive and traumatic to the patient.

One less invasive and traumatic procedure developed more recently is coronary angioplasty. Coronary angioplasty, and angioplasty in general, is a procedure in which a balloon is positioned in the inside of the artery at the site of the accumulation or lesion and inflated in order to dilate the atherosclerotic lesion and thus open the restricted area of the artery. In order to advance the balloon to the lesion, the balloon is attached to the distal end of a small diameter catheter, which includes means for inflating the balloon from the other end of the catheter. The catheter is maneuvered or "steered" through the patient's vessels to the site of the lesion with the balloon in an un-inflated form. When the un-inflated balloon is properly positioned at the lesion, the balloon is then inflated to dilate the restricted area.

While angioplasty has been relatively successful in treating coronary artery disease, restenosis of the treated site often occurs approximately 3 to 6 months following the procedure. It is believed that the primary factor in developing restenosis is the healing that takes place after the injury caused by the intervention of balloon dilation procedure. The restenosis has close analogy to scar formation in that the histologic result has a similar morphology. The histologic response is called intimal fibrous hyperplasia. A main result of the intimal fibrous hyperplasia consists of smooth muscle cells from the vessel wall that proliferate and migrate in the vessel wall. The net result is a thickening of the vessel wall. Over time, this thickening reoccludes or restenosis the vessel to a point where it is clinically significant. That is, the blood flow through the vessel is diminished to a rate similar to the rate before the angioplasty procedure. The occurrence of this seems to happen approximately 30–35% of the time following an angioplasty to that specific site.

Several alternative procedures have been attempted to try to affect the occurrence or rate of the restenosis following intervention to the lesion site in the coronary artery. These procedures have included the use of lasers, mechanical atherectomy devices, heated balloons, and metal implantable stents. While each of these procedures has shown some success in dealing with the initial lesion, all have the similar problem of restenosis at a similar or even greater occurrence. Current estimates of restenosis of the lesion site using these alternative procedures ranges between 40–50%. The time frame of restenosis of all of these is generally from 3–6 months after the procedure.

Therefore, it appears that this restenotic healing lesion area is independent of the type of international procedure used. Rather, it is a physiologic response to any type of injury brought to that lesion site. Because of this intervention independent physiologic response, it is felt by many physicians that potentially the best way to deal with restenosis would be by a pharmacologic means, such as a drug agent, targeted at the biochemical events that take place after injury.

To date, most pharmacologic trials involve either an oral or intravenously injected drug that is delivered throughout the whole body in hopes of trying to effect this small site in the arteries. This type of pharmacologic treatment is known as a "systemic treatment." Some agents that have been tried in human clinicals include: heparin, calcium channel blockers, angiotensin converting enzyme inhibitors, fish oil, and growth peptides. Other agents that may not have been tried in clinicals but are of interest include thromboxane synthetase inhibitor, serotonin antagonists, HMGCoA reductase inhibitors, platelet derived growth factors, inflammatory cell factors, platelet aggregation inhibitors, and thrombin inhibitors such as hirudin or its analogs.

The indication for use of most of these has been either in vitro cell culture studies or animal studies. These studies have shown some effect on the smooth muscle cell proliferation which is a major component of the intimal fibrous hyperplasia that takes place in the restenotic lesion. However, none of the systemic human trials to date has shown a major effect on the occurrence of restenosis.

Even though none of these agents have been completely successful in the in vivo human clinical trials, it is still generally felt that one of these agents or some other new agent, if delivered locally and site specifically to the lesion, would still be able to reduce the proliferative response. One of the problems with systemic techniques is the inability to deliver a high enough concentration of the agent locally at the lesion in order to effect the physiologic response. In the in vitro studies which have shown some success, a high concentration of the agent was used. Thus, it is believed that if the agent was delivered specifically to the site as opposed to systemically, the agent may be delivered at a high enough concentration to truly effect the physiologic response.

The reason many of these agents have not been used in a higher concentration in vivo in humans is that many of the agents may exhibit undesirable side effects. Thus, if a high concentration of the agents is given systemically, they may have unwanted physiologic effects. Therefore, if the drug can be given with high concentrations locally to the vessel wall while minimizing the systemic amount of drug, the desired result of modulating the restenotic growth while preventing any unwanted systemic effects may be achieved.

There are other ways known to date in trying to create a site specific local delivery of drug to a site. One approach presently contemplated is the use of a perforated or sweating balloon. For example, a drug delivery device is disclosed by Wolinsky, H., et al. in the article entitled, *Use of a Perforated Balloon Catheter to Deliver Concentrated Heparin Into the Wall of a Normal Canine Artery*, 15 JACC 475

(February 1990). This device is a percutaneous transluminal coronary angioplasty (PTCA) balloon with several microholes in the balloon for delivery of an agent during balloon dilatation. The drug is incorporated into the same fluid which is used to inflate the balloon.

A major concern with any device with perforated holes is the effect of a jet stream on the wall of the blood vessel. If a balloon with holes is pressurized, a relatively high velocity and/or pressure jet stream may be ejected through the holes. There are some indications that these jet streams may cause tissue damage resulting in very severe dissection of the vessel wall after the dilatation procedure.

Another disadvantage of available devices, such as the one disclosed by Wolinsky et al., is that these devices cause a substantial blockage of blood flow in the subject vessel during the procedure. Thus, such devices may only be used for the fairly short time frame (typically, from one to two minutes), similar to the time frame of the actual angioplasty dilatation.

Other available drug delivery devices are disclosed, for example, in U.S. Pat. Nos. 4,824,436 (Wolinsky) and 4,636,195 (Wolinsky). These devices are directed to a dual occlusion catheter in which a balloon is inflated proximally and distally of the accumulation or lesion creating a space for infusion of a drug. This dual balloon catheter creates a space for infusion of drug separate from the blood flow. This device, however, also can only be used for a short period of time because it occludes blood flow.

Perfusion is very important in developing a suitable type of delivery device. It is necessary that the device provide a large latitude in time over which the agent could be delivered and therefore, devices which occlude blood flow may not provide the necessary latitude. Because the basic research into the biochemistry and physiologic events indicate that the initial events begin immediately after injury and continue intensely for several hours, it is desirable for the drug delivery system to allow drug delivery for several hours to a day or two beginning immediately after intervention. This research also points out that the initial events subsequently create a cascade of events that ultimately lead to intimal thickening. While these accumulations or lesions do not become apparent for several months, it is felt that if these initial events can be modulated, blocked, or even accelerated, then the subsequent cascade can be altered and a diminished overall thickening could be achieved.

Even in devices where the shaft tubing provides a lumen for blood flow, the blood flow is limited by the diameter of the tube. In fact, when the shaft tubing is used for a blood flow lumen, there is a competing balance of making the shaft large enough to accommodate the larger volume of blood flow while still trying to minimize the size so that the catheter can be maneuvered through the patient's vasculature. This limited blood flow, while providing obvious advantages to no blood flow, may not be completely satisfactory in providing the necessary blood flow to the heart (or other part of the body).

Catheters with expandable devices are also used in other procedures. For example, U.S. Pat. No. 4,183,102 (Guiset) discloses a device which includes a series of toroidal shaped sleeves which conform to a vessel wall. The device disclosed in this patent is for the treatment of some aortic aneurysms and does not include any means for drug delivery.

Therefore, it is desirable to have a drug delivery device capable of providing the necessary blood flow to the heart for restenosis treatment. Further, such a device may also be extremely desirable in other procedures where a drug is to be delivered to a specific site in a vessel. For example, drug delivery devices may be useful in procedures where a drug or agent is used to dissolve the stenosis in an effort to avoid the use of angioplasty or atherectomy procedures altogether or to deliver a thrombolytic agent to dissolve a clot at the lesion site.

It will be recognized from this discussion that there is a need for a genetic type of drug delivery system which emphasizes physician control over the device and agent. The device should have flexibility as to the agent that is to be delivered and should be capable of delivering any number of agents (either separately or at the same time), or possibly also allow a change in the protocol of the delivery. It should also be flexible with respect to the time frame over which these agents would be delivered. In order to effect this time frame of delivery, the device should also allow a large amount of blood flow by or through the device in order to maintain adequate distal perfusion of cardiac or other muscle during the delivery time.

Therefore, it is a primary object of the present invention to provide a device and method which can contain a relatively high concentration of a drug agent in a selected potion of a vessel, such as a blood vessel.

It is another object of the present invention to provide a device which can be used in a flexible time frame.

It is a further object of this invention to provide a drug delivery catheter which permits a relatively high fluid flow rate through the vessel in which it is inserted while the device is employed.

It is a still further object of this invention to provide a device which is flexible as to the drug and the number of drugs which can be delivered as well as the time frame over which they can be delivered.

SUMMARY OF THE INVENTION

To achieve these and other objects, the present invention provides a new and unique drug delivery catheter which may be inserted into a vessel, such as a blood vessel. The drug delivery catheter of the present invention comprises an elongated tubular shaft which includes a drug lumen for delivering a drug to the treatment site and a uniquely configured inflatable balloon assembly. The balloon assembly is disposed at the distal end of the shaft and includes an inflatable balloon member. The balloon member has a configuration such that when the balloon member is uninflated, the fluid in the vessel (such as blood) may flow around the balloon assembly. This provides an arrangement which may be easily inserted and manipulated through the vascular system. When the balloon member is an inflated state, part of the balloon member contacts the vessel wall defining a containment pocket between the vessel wall and the balloon assembly. The balloon assembly includes apertures in the containment pocket which are in fluid communication with a drug lumen in order to provide the drug to the containment pocket. A flow lumen is also defined through the balloon member when it is inflated in order to allow the fluid in the vessel, such as blood, to flow through the balloon assembly. The catheter also includes an inflation lumen which is used to inflate the balloon member.

The present invention also encompasses a method of using the drug delivery catheter to deliver drugs to a treatment site in desired concentrations.

The present invention provides a time frame for drug delivery in relatively high concentrations and which can be used in a relatively flexible time frame. For example the time frame may be greater (or less) than several minutes to possibly several hours or a day to two days.

This time frame of delivery is important in procedures intended to abate the occurrence of restenosis because the time frame needed to favorably modulate the restenotic response is variable.

Further, the device and method of the present invention may be advantageously used to deliver a drug agent intended to dissolve a lesion or to dissolve a clot at a lesion site.

BRIEF DESCRIPTION OF THE DRAWINGS

FIG. 1 shows an embodiment of the drug delivery catheter of the present invention.

FIG. 2a shows a cross section of the embodiment of FIG. 1 along line 2a—2a.

FIG. 2b shows a cross section of the embodiment of FIG. 1 along line 2b—2b.

FIG. 3a shows a cross section of the embodiment of FIG. 1 along line 3a—3a.

FIG. 3b shows a cross sectional slice of the embodiment of the device of FIG. 1 in a plane perpendicular to line 3a—3a.

FIG. 6 shows another embodiment of the drug delivery catheter of the present invention.

FIG. 7 shows another embodiment of the drug delivery catheter of the present invention.

FIG. 9a shows a cross section of the embodiment of FIG. 9 along line 9a—9a.

DETAILED DESCRIPTION OF THE PREFERRED EMBODIMENT

Figure 4:
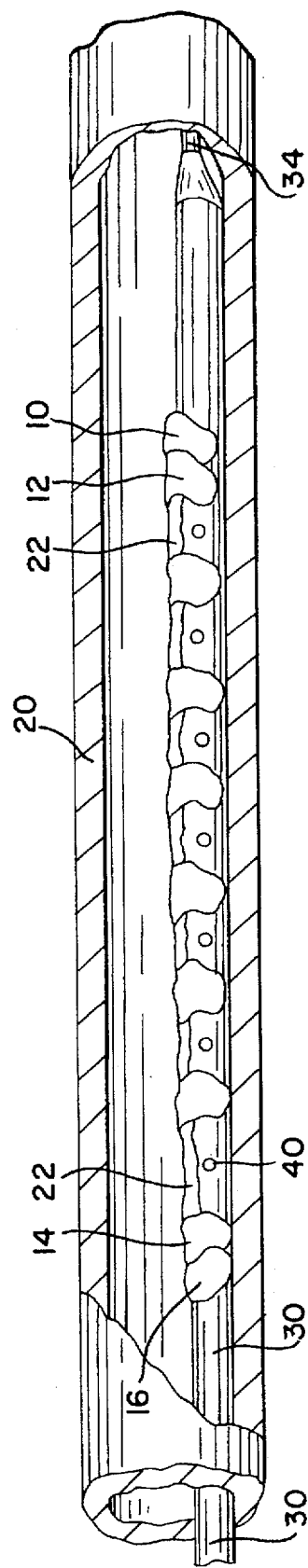
FIG. 4 shows another embodiment of the drug delivery catheter of the present invention in a deflated form.

Referring to FIGS. 1, 2a, 2b, 3a and 3b, a preferred embodiment of the present invention includes a balloon assembly comprising a single piece of balloon tubing laced in a manner that will be described below to form toroidal or donut-shaped balloons 10, 12, 14, 16. When inflated the balloons 10, 12, 14 and 16 are intended to impinge upon or engage the vessel wall 20 as explained in more detail below. The figures depict the balloons 10, 12, 14, 16 in their inflated form.

In an exemplary embodiment, these balloons 10, 12, 14, 16 are about 3 millimeters (mm) in outside diameter in their inflated form. The balloons, however, can have an outside diameter ranging from about 2 mm to about 20 mm in their uninflated form, depending on the different vessels of the human (or animal) body in which the balloons will be used. The size of the balloons may also vary for different procedures.

The most distal balloon 10 and the next most distal balloon 12 are preferably adjacent to each other as are the most proximal balloon 16 and the next most proximal balloon 14. The distance between the next most proximal balloon 14 and the next most distal balloon 12 may be, for example, about 20 mm.

Providing the balloons in pairs advantageously provides two points of anchoring for each pair. This is particularly useful at the ends of the balloon assembly where the two point anchoring reduces the tendency of the balloons to rotate perpendicular to their axis.

The balloons are preferably made of a polyolefin. A suitable polyolefin material is available from E. I. DuPont de Nemours and Co. (Wilmington, Del.) under the tradename Surlyn® Ionomer.

The balloon assembly also includes a cylindrical sheath 22 which connects the balloons 10, 12, 14 and 16. The diameter of the sheath 22 is less than the diameter of the balloons. Therefore, when the balloons are inflated, the sheath 22 is attached to the balloons at a point radially inward of the outer diameter of the balloons in order to create a pocket. Preferably, the sheath 22 is disposed through and connected to the interior portion of the toroidal-shaped balloons. In an exemplary embodiment, the sheath 22 is typically 25 mm from end to end longitudinally and is preferably about 0.001 inches thick.

The sheath 22 is situated coaxially to the vessel wall 20 and is open at each end, thereby forming a passageway or blood lumen 24 for the blood to flow through when the balloons are inflated. Thus, the sheath 22 creates a barrier for separation of the drug medium and the blood. The sheath 22 is supported or held open by the toroidal-shaped balloons 10, 12, 14, 16 and has the capability of having a relatively large internal diameter. For example, the internal diameters may be about 0.060 inches providing a very large volume of blood flow. This internal blood flow lumen 24 formed by the sheath 22 has the capability of being significantly larger than the shaft tubing of the device.

The sheath 22 may be made of Surlyn® Ionomer. More preferably, the sheath 22 may be made of a polyester copolymer such as a random copolymer. The random copolymer used to make the sheath of the present invention may be prepared according to standard procedures from ethylene glycol, and a mixture of dimethyl terephthalate and dimethyl isophthalate. As used in the random copolymer, the ratio of terephthalate to isophthalate in the random copolymer may be varied over the range of between 99:1 to 80:20. Suitable copolymers are commercially available and are sold under the tradename Selar® PT, such as Selar® X257, available from E. I. Dupont de Nemours and Company (Wilmington, Del.).

In this embodiment, the blood flow lumen 24 is created by the inflation of the balloons 10, 12, 14, 16 and can be subsequently collapsed upon deflation of the balloons 10, 12, 14, 16 (FIG. 4 illustrates the balloons in a deflated state). The dimensions of the deflated device will, of course, vary depending on the specific use contemplated, but suitable sizes range from 0.035 inches to 0.1 inches.

Figure 5:
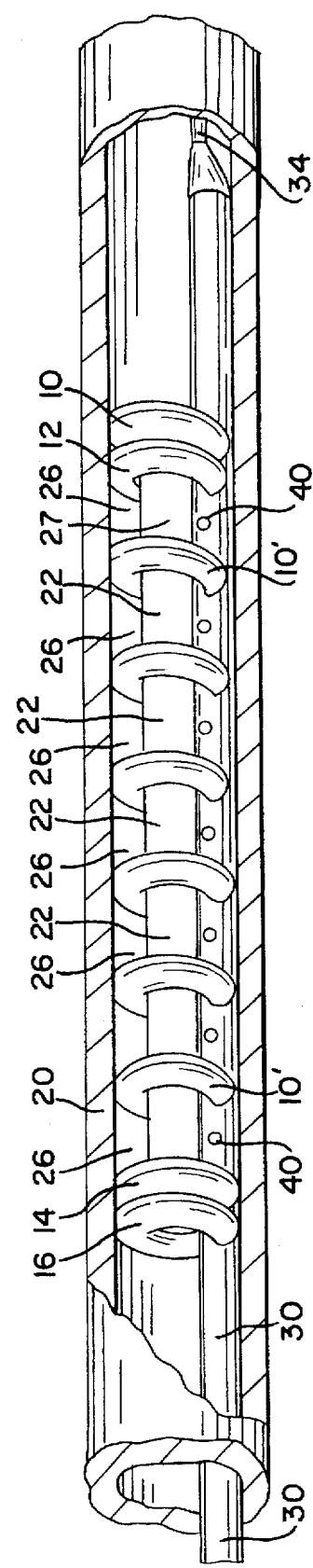
FIG. 5 shows the embodiment of the drug delivery catheter of FIG. 4 in an inflated form.

As illustrated best in FIGS. 1 and 5, when the balloons are inflated, a containment pocket or region 26 is defined between the sheath 22 and balloons 12, 14 and the vessel wall 20. When the balloons 12, 14 are inflated they in effect form a seal between the vessel wall 20 and the balloons 12, 14 and thus the balloons 12, 14 define the outer boundary of the containment pocket 26. The sheath 22, which is bonded to the balloons 12, 14, defines the rest of the containment pocket 26. This containment pocket 26 provides region in the vessel which is isolated or separate from the fluid flowing through the flow lumen 24. Therefore, the drug medium may be contained in this containment pocket 26 in the desired concentrations for a predetermined period of time without entering the blood stream for that period of time.

The backbone of this embodiment is a catheter (or shaft) formed by an elongated tubular shaft 30 into which the balloon tubing is laced in a manner that will be described in detail below to form the toroidal or donut-shaped balloons 10, 12, 14, and 16. The specific size and configuration of the shaft tubing 30 will, of course, vary depending on the specific application for which it is intended. In one exemplary embodiment, the shaft tubing is about 135 centimeters (cm) long, about 0.040 inches in distal outside diameter and about 0.050 inches in proximal outside diameter, and has a wall thickness of from about 0.003 inches to about 0.004 inches. The diameter of the tubing 30 can range from about 0.030 inches to about 0.090 inches depending on the contemplated use. These exemplary dimensions are suitable for a catheter intended for use in the coronary arteries. As will be recognized, the dimensions for catheters intended for use in the prostate, urethra, etc. may have other suitable dimensions. This shaft tubing 30 is preferably made of a flexible material such as a high density polyethylene (HDPE).

The shaft tubing 30 is advantageously necked at its distal end to allow for variable stiffness or variable flexibility along the shaft. The necking of the shaft tubing 30 may be implemented by several arrangements. For example, a necked region, that is a region which is more flexible than the rest of the tubing, may be provided by reducing the outer diameter of the tubing, by reducing the wall thickness of the tubing, or by providing a section of the tubing made of a more flexible material than the rest of the tubing. The necked portion may also be provided by any combination of these techniques.

FIG. 3b best illustrates this necking in one preferred embodiment. FIG. 3b depicts a slice through the plane perpendicular to the plane of FIG. 3a and for purpose of clarity does not depict the structure of the device which is not in this plane. The shaft tubing 30 is bonded to a necked section 30a of proximal shaft tubing. The bonding 152 commercially may be accomplished with an adhesive, such as BiPax® BA-2135D Tra-Bond available from Tra-Con (Medord, Mass.). The necked section 30a of proximal shaft tubing may have, for example, an outside diameter of about 0.040 inches and a wall thickness of about 0.003 inches. Proximal to the necked section 30a of proximal shaft tubing, there is a transition section 31 followed by the unnecked section 30b of proximal shaft tubing 30. The unnecked section 30b may have an outside diameter of about 0.050 inches and a wall thickness of about 0.004 inches.

By way of example, the shafting tubing 30 may be about 135 cm long, the necked section 30a of proximal shaft tubing may be about 25 cm long, and the unnecked section 30b of proximal shafting tubing may be about 110 cm long. Preferably, the shaft tubing 30 has a tapered section 33 at its distal end to prevent damage to the vessel walls as it is being inserted.

A necking may be accomplished by pulling the tubing through a heated die to elongate it and therefore change its inside and/or outside diameters.

An inner shaft tubing 32 runs coaxially through the shaft tubing 30 in order to accommodate a PTCA guide wire 34. This type of guide wire is known in the art and therefore no further discussion is given here. A suitable configuration for the inner shaft tubing 32 is a flexible tube made of HDPE which is about 135 cm long, and has a wall thickness of about 0.003 inches.

This inner shafting tubing 32 may also be necked to provide added flexibility to the catheter. As illustrated in FIG. 3b, in one exemplary embodiment the inner shafting tubing 32 has a transition region and an unnecked proximal portion 32b. The distal, necked portion of the inner shaft tubing 32 may be about 0.021 inches in outside diameter and about 30 cm long. The unnecked proximal portion 32b may be about 0.024 inches in outside diameter and about 105 cm long.

The necked or more flexible potion of the catheter may be provided by necking one or both of the shaft tubing 30 and the inner shaft tubing 32.

A more detailed discussion of the arrangements and advantages of necking are disclosed in U.S. Pat. No. 4,976,690 (Solar et al.) which is incorporated herein by reference.

As illustrated there are basically three different lumens through the proximal portion of the shaft tubing 30, one being the inner lumen for the guide wire 34 formed by the inner shaft tubing 32, another being an inflation lumen 36 for the balloon inflation medium which is continuous with the donut-shaped balloons 10, 12, 14, 16 (described in greater detail below), and the final one being the drug delivery lumen 38 formed in the space between the inner shaft tubing 32 and the shaft tubing 30.

In one exemplary embodiment, the inflation lumen is made at its distal end (where the balloons 10, 12, 14, 16 are formed), from Surlyn®, and has an inside diameter of 0.006 inches and an outside diameter of 0.011 inches.

In a presently preferred embodiment the inflation lumen is formed of three sections: 1) the section attached to the balloons described above; 2) a middle inflation lumen section 164; and 3) the proximal inflation lumen section 166 which eventually is attached to the manifold (not shown). Both the middle and proximal inflation lumen sections 164, 166 are preferably made of a polyimide material. The bond 170 of the balloon tubing 36 to the middle inflation lumen section 164 and the bond of 172 of the middle inflation lumen tubing 164 to the proximal inflation lumen tubing 166 is accomplished with a suitable adhesive, such as Loctite® 405 available from Loctite Corp. (Newington, Conn.). The middle inflation lumen section 164 may have an inside diameter of about 0.012 inches, a wall thickness of about 0.001 inches, and may be about 25 cm long. The proximal inflation lumen section may have an inside diameter of 0.016 inches, a wall thickness of 0.001 inches, and may be about 100 cm long. It will be recognized that these dimensions are given by way of example and other suitable sizes may be employed.

The shaft tubing 30 has a number of apertures 40 in order to accommodate the drug flow out of these apertures 40 into the containment pocket 26 formed between the two inner balloons 12, 14, the sheath 22, and the vessel wall 24. The apertures 40 are placed longitudinally along the shaft tubing 30 between the inner most balloons 12, 14. The apertures 40 are on both sides of the shaft tubing 30 and the area in which they are placed does not come into contact with the vessel wall 20. Preferably, the apertures 40 generally increase in diameter from proximal to distal end so that uniform flow out of each aperture 40 is achieved. The apertures are preferably sized such that the drug medium is not pressure injected out of the apertures 40, but rather the vessel tissue is "bathed" with the drug medium. The size of the apertures will, of course, depend on the pressure at which the drug medium is being provided at the proximal end by the drug medium source (not shown). In an exemplary embodiment, the more proximal apertures 40 are about 0.003 inches in diameter and the more distal apertures are about 0.005 inches in diameter. These apertures 40 are placed about 2 to 3 mm apart from each other.

This embodiment is manufactured by drilling the apertures into the shaft tubing 30 and then lacing non-blown balloon tubing 36 through these apertures in such a way that the tubing is looped around a temporary forming mandrel (not shown) to form the section in which the sheath will be placed. Upon completion of this lacing, the tubing is pressurized and dipped into a hot water bath, preferably at 80° C., for expansion of the thermoplastic balloon tubing 36 to form the outer, donut-shaped balloons 10, 12, 14, 16.

After this process, another thin-walled cylindrical balloon is inserted into the interior of the toroidal or donut-shaped balloons 10, 12, 14, 16 to form the sheath 22 which separates the drug and blood mediums. The sheath 22 is then bonded to all of the donut-shaped balloons 10, 12, 14, 16 and the ends are cut off flush to the most proximal and distal donut-shaped balloon 10, 16. The bonding may be accomplished by the use of a suitable adhesive, such as an epoxy resin with an aliphatic amine hardener. The formulation for a suitable epoxy is given below in Table 1.

TABLE 1

(EPOXY ADHESIVE)

| | Wt. (in grams) | Epoxide Equivalent Wt. | Description |
|---|---|---|---|
| Araldite GY 508 [Ciba Geigy] | 148.8 (g) | 400–455 | Bisphenol A based epoxy blended with polyglycol diepoxide |
| Araldite GY 506 [Ciba Geigy] | 59.0 (g) | 172–185 | Bisphenal A based epoxy |
| Epon 828 (Shell) | 92.6 (g) | 187.5 | Bisphenal A based epoxy |
| 2-Methyl-1,5-pentadiamine (Dytek A from Dupont) | 32.5 (g) | | |

The inner shaft tubing 32 is then put through the shaft tubing 30 in order to accommodate a guide wire 34. This inner shaft tubing 34 is fastened to the manifold on the proximal end of the catheter with an adhesive bond, such as a urethane adhesive bond available from the 3M Company (Minneapolis, Minn.) under the tradename designations Scotch Weld® Brand 3549 B/A Urethane Adhesive Kit. The inner shaft tubing 32 is fastened to the outer shaft 30 on the distal end of the catheter using the same urethane adhesive. This bonding material on the distal end may also be used to form the tapered section 33.

As is illustrated in FIG. 3a, the toroidal-shaped balloons 10, 12, 14, 16 are formed from one continuous piece of tubing since they are laced through the shaft tubing 30 and therefore the balloons 10, 12, 14, 16 are all in fluid communication with each other.

The proximal end of this catheter comprises a manifold (not shown) known in the art. A suitable manifold is a conventional three-port manifold. A vacuum source is placed on the balloon inflation port of the manifold to evacuate air from the balloons. The drug infusion port of the manifold is then filled with a sterile liquid to evacuate air.

Thus, the blood flow lumen 24 is not an integral part of the shaft of the device. Rather the lumen is created by inflation of the balloons 10, 12, 14, 16 of the device. Since the blood flow lumen 24 is not an integral part of the shaft, the ultimate diameter of the blood flow lumen 24 is not kited by the diameter of the shaft. When the balloons 10, 12, 14, 16 are deflated, the device is collapsed with essentially no blood flow lumen and therefore small enough in diameter to easily maneuver through the patient's vascular system. As discussed above, in some prior art devices, the lumen was created by the shaft tubing itself thereby limiting the size of the blood flow lumen. Unlike prior an devices, when the balloon member is inflated, the cross-sectional area of the blood flow lumen 24 is a significant percentage of the cross-sectional area of the blood vessel. It is presently believed that with the present invention, the blood flow through the device will be about 60% and may be as much as 80% of the blood flow through a healthy vessel without the device in place.

Significantly, in this embodiment the balloon inflation medium, which may be any suitable inflation medium such as saline and contrast dye, is separate from the drug medium. This separation is important because it provides flexibility as to the amount of drug delivered, the time frame over which it is delivered as well as flexibility as far as deployment of the device. Also, as will be recognized by those skilled in the art, this embodiment minimizes the problem of tissue damage caused by a very high jet stream of the drug being ejected from the catheter. As mentioned above, preferably the apertures 40 are not directed toward the vessel wall 20 and the apertures 40 are appropriately sized such that the drug emerges from the apertures to the wall in a slow gentle stream instead of emerging from the apertures 40 in a pressurized stream. Thus, the containment region 26 created between the shaft tubing 30 and the vessel wall 20 is used to "bathe" the vessel wall 20.

Other embodiments of the present invention are illustrated in FIG. 4, FIG. 5, FIG. 6, and FIG. 7 with elements similar to the previous embodiment numbered similarly. FIGS. 4 and 5 illustrate this device in the blood vessel 20 both deflated (FIG. 4) and inflated (FIG. 5). As illustrated in these figures the balloons in the balloon assembly may be spaced differently and additional balloons may be placed at closer intervals. The additional balloons will aid in keeping the perfusion lumen open. The configuration and positioning of the toroidal-shaped balloons have multiple possibilities. More balloons may be formed between the previously-described toroidal-shaped balloons 10; and the balloons 12 and 16 may even be eliminated. (FIG. 7). For all of these embodiments, the distance from the most proximal balloon 16 to the most distal balloon 10 can range from about 20–30 mm and the inside balloons 10' may be disposed about 2–3 mm apart.

The number of balloons and the spacing between balloons is important in maintaining the appropriate blood flow through the vessel being treated. It is possible that the flow of blood through the sheath 22 may be cut off by any one of the following: (1) the lesion may deform the sheath; (2) the device may be placed at a bend and the sheath could kink; and/or (3) the pressure of the drug could force the blood lumen shut. Therefore, the radial support needed for the sheath 22 will vary depending on the specific conditions of the treatment site and the particular treatment being administered. The radial support for the sheath 22 needed to maintain the blood flow lumen 24 through the center of the sheath 22 is provided by the balloons. The different configurations illustrated may be used to provide more or less radial support as needed. Increasing the number of balloons in the balloon assembly increases the ability of the balloon assembly to maintain the perfusion lumen open.

Figure 8:
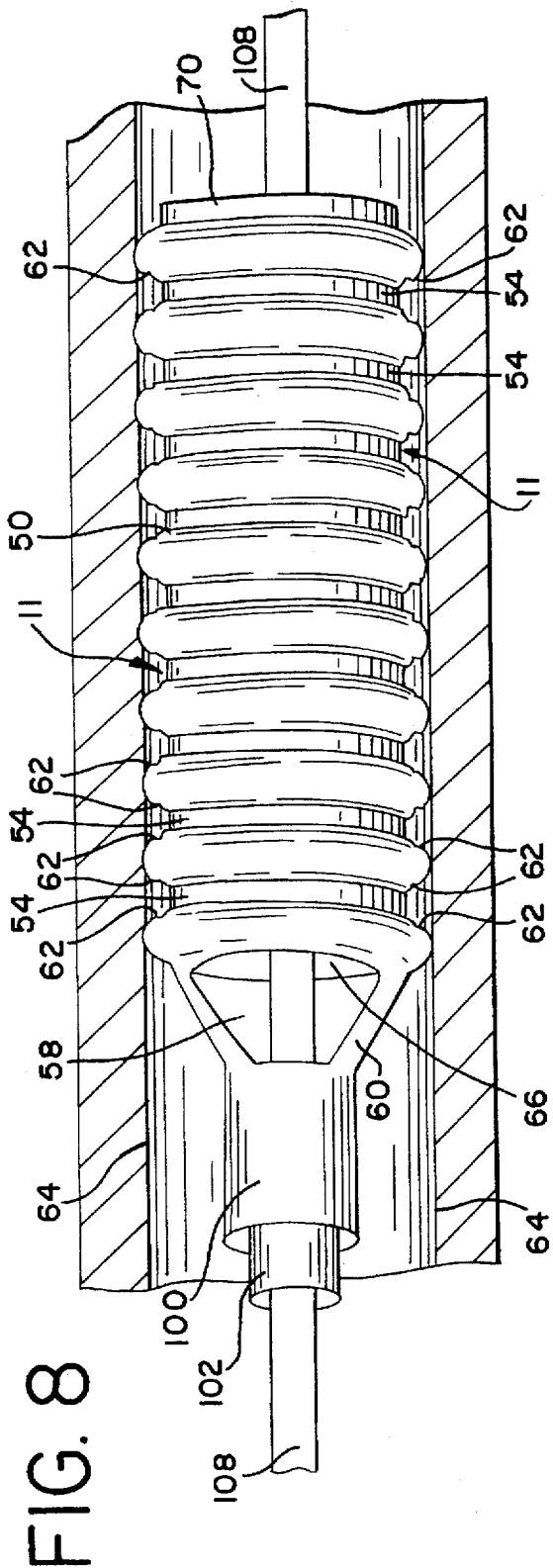
FIG. 8 shows another embodiment of the drug delivery catheter of the present invention.
Figure 8B:
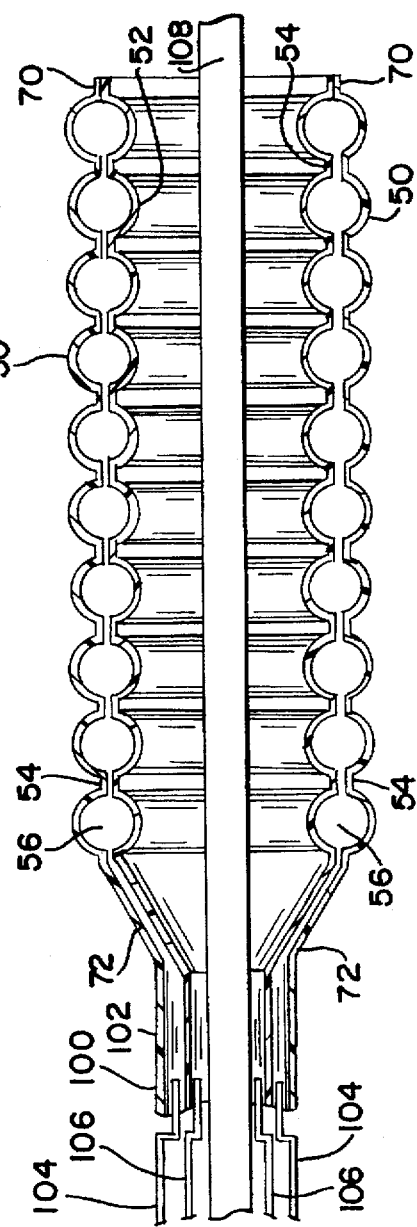
FIG. 8b shows a cut-away view of the embodiment of FIG. 8.
Figure 8A:
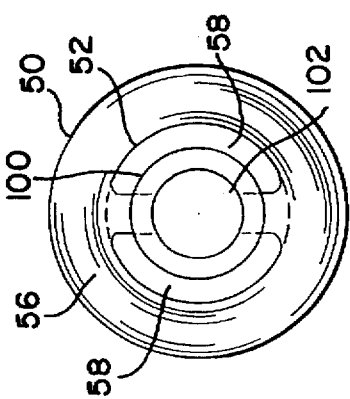
FIG. 8a shows a front view of the embodiment of FIG. 8.

Referring now to FIGS. 8, 8a, and 8b, another embodiment of the inventions is shown. In this embodiment the balloon assembly is comprised of an outer cylindrical sheath 50 and an inner cylindrical sheath 52 sealed to each other at the ends of the sheaths. The cylindrical sheaths 50 and 52 are also intermittently sealed to one another at sections 54. An inflation region or pouch 56 is defined between the two sheaths 52 and 54. These seals 54 run along the circumference of the cylindrical sheaths 50, 52 except that they are not complete in that spaces are left at certain points to allow the inflation medium to migrate from one pouch formed between the cylindrical sheaths 50, 52 to another similar pouch. The method for forming these seals is discussed in greater detail below.

Cutouts 58 are provided in the proximal cone section 60 of the sheaths to allow blood to flow through the center of these sheaths 50, 52. At the proximal portion of the cone, the outer sheath 50 and the inner sheath 52 come to an outer balloon waste 100 and an inner balloon waist 102. The outer balloon waist 100 is bonded with an adhesive, such as Tracon®, to an outer-shaft 104 and the inner balloon waist 101 is bonded with a similar adhesive to an inner shaft 106. The outer and inner shafts are made in a similar fashion to the embodiments previously described. The inner shaft 106 defines a lumen for a guide wire 108. The space between the outer and inner shafts 104 defines the drug/inflation medium lumen.

The double sheath/balloon assembly may be formed for example from commercially available PTCA catheter balloons. The outer sheath 50 and an inner sheath 52 are, however, may also be made from a polyester copolymer such as that described above.

In an exemplary embodiment the outer sheath 50 and inner sheath 52 are about 2.9 mm and about 3.0 mm respectively in outside diameter. Depending on the use, however, these diameters may range from about 1.9 mm and about 2.0 mm to about 5.5 mm and about 6.0 mm, respectively. The sheaths 50, 52 are preferably about 20 mm in length, but may vary from about 10 mm to about 30 min. The length of the total device is approximately 135 cm, but may range from about 75 to about 150 cm. The seals 54 may be between about 0.005 inches and 0.01 inches wide and about 2 mm away from each other, though other configurations may be employed.

In this embodiment, the inflation medium and drug medium are one and the same. When the balloon assembly is inflated, as shown in FIGS. 8–8b, the outer sheath 50 contacts the wall of the vessel 64 at the areas designated by reference numeral 63. The contact area 63 is defined by the section of the sheath 50 which is not bonded to the other sheath 52. The area 54 where the two sheaths 50, 52 are bonded, however, does not contact the vessel wall 64. Therefore, a containment pocket or region 11 for the drug is defined in the space between two adjacent contact areas 63. The outer sheath has apertures or holes 62 in order to deliver the drug to the vessel wall 64 in the containment pocket 11. These apertures 62 allow for permeability of the inflation medium (which contains the drug) out to the vessel wall 64. Preferably, these apertures 62 are about 0.003 inches in diameter and spaced radially at 90° for each pouch. Here again other configurations may be suitable as well. For example, both the number and pattern of spacings of the apertures in each pocket defined by adjacent ribs may vary. The polymer that the outer balloon is formed of can either have the apertures 62 as discussed above or alternatively may be semi-permeable to the inflation/drug solution.

This embodiment also provides very good separation of drug from the blood lumen and excellent blood flow because the blood flow lumen 66 is created by the inflation and expansion of the double sheath 50, 52 balloon assembly. The sheaths 50, 52 are inserted into the patient in a deflated form (not shown) and when they are positioned properly, they are inflated until the outer balloon 50 comes into contact with the vessel walls 64. The details for using this embodiment are similar to those described below for the embodiment of FIGS. 1, 2a, 2b and 3.

Similar to the other embodiments discussed above, the position and number of inflation pouches 56 may vary for different uses. To accomplish this, the seals between the two cylindrical sheaths 50, 52 can have different configurations depending on what type of lifting and expansion force would be needed.

This embodiment of FIGS. 8, 8a, and 8b, is preferably made by blowing two different sheaths 50, 52, one slightly smaller than the other 52. The second smaller inner sheath 52 is inserted coaxially inside the outer sheath 50. These are then completely sealed distally, creating an occlusive seal 70 between the two sheaths 50, 52. These two sheaths 50, 52 may have intermittent seals through the body of the balloon assembly similar to what an inflatable air or water mattress would have; these seals are incomplete in places, allowing the inflation medium/drug to flow throughout the device. In an exemplary embodiment, the seals are 2–3 mm apart with a 0.01 inch wide bond. On the proximal end in the cone area 60 of the sheaths 50, 52, there are sealed cutaway portions 58 for blood flow. This sealing is around the cutaway portions 58 and allows the blood to flow while still maintaining inflation space 72 in parts of the cone to the body of the cylindrical sheaths.

The sealing can be done in a number of different ways. One preferred method is by creating a heat seal between the two sheaths. This heat seal can be made by a laser weld, a radio frequency weld, or an ultrasonic weld. Other equivalent methods can be substituted. In each case, the polymer of the two cylindrical sheaths would be heated very locally to form a heat bond between the two pieces of the polymer.

Figure 9:
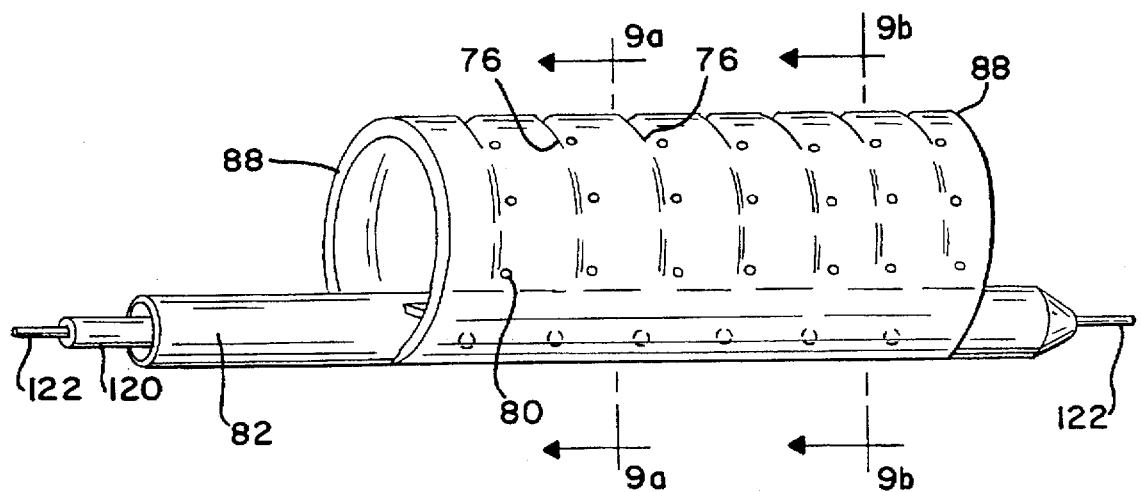
FIG. 9 shows another embodiment of the drug delivery catheter of the present invention.
Figure 9A:
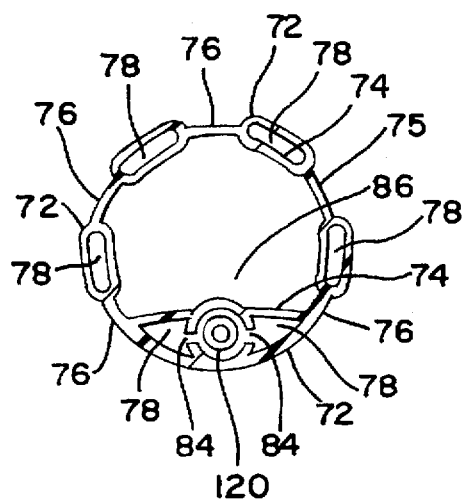
Figure 9B:
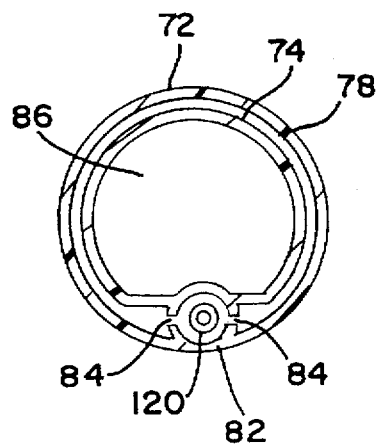
FIG. 9b shows a cross section of the embodiment of FIG. 9 along line 9b—9b.

Referring now to FIGS. 9, 9a, and 9b, another embodiment of the invention is shown. FIG. 9a shows a cross section of FIG. 9 along line A—A' and FIG. 9b shows a cross section of the embodiment of FIG. 9 along line B—B'. This embodiment is comprised of an outer polymer cylindrical sheath 72 and an inner polymer cylindrical sheath 74 intermittently sealed to one another at areas 76 to form a balloon assembly with an inflation area 78 being defined between the two sheaths 72 and 74. This embodiment is similar to the embodiment of FIGS. 8, 8a, and 8b except the seals in the balloon assembly are intermittent forming welds which are similar to spot welds.

In an exemplary embodiment, the outer sheath 72 and inner sheath 74 are about 2.9 mm and about 3.0 mm respectively in outside diameter and about 0.001 inches thick. In an exemplary embodiment, the balloon assembly comprised of sheaths 72, 74 is about 20 mm long and the total device is preferably about 135 cm long. The total device length, however, may range from about 75 to about 150 cm long. The outer sheath 72 and an inner sheath 74 are preferably made from the above-mentioned Selar® copolymer. The seals 76 are approximately 0.005 inches wide and approximately 1–2 mm from each other. The method for forming these seals is similar to the methods discussed in greater detail above.

The inflation/drug medium is delivered into the balloon assembly, which comprises the sheaths 72, 74, through shaft tubing 82 that runs longitudinally along the device. Again, in this embodiment, the inflation medium and drug medium are one and the same. There are apertures or holes 80 put into the outer sheath in order to deliver drug to the vessel wall. These apertures 80 allow for permeability of the inflation medium (which contains the drug) out to the vessel wall in a containment pocket defined between adjacent areas where the outer sheath contacts the vessel wall. A suitable diameter for these apertures 80 is about 0.003 inches. Apertures 84 in the shaft tubing 82 allow the inflation medium/drug to pass from the shaft tubing 82 to the space 78 between the sheaths 72, 74. These apertures 84 are 0.01 inches in diameter, 0.50 mm apart and run longitudinally along the shaft tubing 82. The shaft tubing 82 may also be necked to provide variable stiffness along the length of the shaft.

In an exemplary embodiment, this shaft tubing 82 is about 135 cm long, about 0.040 inches in outside diameter, semi-rigid yet flexible, and preferably made of HDPE.

An inner shaft tubing 120 runs coaxially through the shaft tubing 82 in order to accommodate a guide wire 122. The guide wire 122 may be a PTCA guide wire as is known in the art. In one exemplary embodiment, this inner shaft tubing 120 is also flexible, about 135 cm long, about 0.021 inches in distal outside diameter, about 0.024 inches in proximal outside diameter, has a wall thickness of about 0.003 inches, and is made of HDPE. This inner shaft tubing 120 may also be necked as described above.

Similar to the other embodiments described above, the position and number of inflation pouches and/or seals can have multiple configurations depending on what type of lifting and expansion force would be needed.

This embodiment may be made by blowing two cylindrical sheaths 72, 74, one slightly smaller than the other 74. The second smaller inner sheath 74 is inserted inside the outer sheath 72. The sheaths 72, 74 are then completely sealed proximally and distally at section 88, creating an occlusive seal between the two sheaths 72, 74. These two sheaths 72, 74 may have intermittent seals 76 through the body of the balloon similar to what an inflatable water mattress would have. The sealing can be formed in a number of different ways as described above.

This embodiment also provides good separation of the drug from the blood flow lumen and excellent blood flow because the blood flow lumen 86 is created by the inflation and expansion of the double sheath 72, 74 sleeve/assembly. The balloon assembly is inserted into the patient in a deflated or collapsed form (not shown) and when positioned properly, it is inflated until the unsealed sections of the outer balloon wall 72 come into contact with the vessel wall. Again, details for the use of this embodiment are similar to those described below for other embodiments.

With all of the embodiments disclosed above, because the blood flow lumen is created by the inflatable balloon assembly (which may consist of any or all of a balloons/sheath/shaft/etc.) the overall device can be kept to a minimal size. The blood flow lumen is only formed upon inflation of the balloon assembly and the device is in effect collapsed in its uninflated form. This physical attribute allows the catheter to be of a very small diameter when it is inserted into the patient's body and maneuvered to the desired position, yet provides a relatively large blood flow lumen when the balloon member is inflated. Unlike prior art devices the blood flow lumen is not formed by solid tubing, but instead by an inflatable and collapsible means. Since blood is not flowing through the shaft of the device like prior art devices, the competing balance of minimizing the size of the device and making the shaft large enough to accommodate the larger volume of blood flow is eliminated. In all of the embodiments disclosed, it is presently believed that when the device is inflated the flow will be at least 60% of what the flow would be without the device in place. Additionally, the drug may be delivered to a pocket which is separate or isolated from the blood flow. This permits the drug to be administered at higher concentrations and locally at the selected treatment site in the blood vessel.

A preferred use for this device is a method of treating the vessel wall after PTCA and the following description of the use of the invention after PTCA is given so as to provide a practical example of the procedure for using the present invention. One skilled in the art, however, can envision many other uses of the invention for delivering drugs to blood vessel walls or to walls of other ducts or cavities. The following example is given with respect to the embodiment of FIG. 1. It will be recognized that similar procedures will be used with respect to other embodiments of the invention.

Before use, the drug delivery catheter of the present invention must be prepared. First vacuum is pulled on the balloon inflation port of the manifold to evacuate any air from the balloons. Then the drug infusion port is filled with a sterile liquid, again to evacuate air therefrom.

Following a typical well known PTCA procedure, the drug delivery catheter of the present invention is exchanged over the existing guide wire 34 used in the PTCA. The drug delivery catheter is slid over the guide wire 34 and positioned at the same site as the balloon dilation was performed. The balloons are then inflated to between 5 and 10 atmospheres such that the containment region is defined as explained above. Drug infusion is then initiated through the apertures in the balloon assembly to provide the desired drug to the containment pocket or region and thus to the vessel wall. The drug or agent is provided in a therapeutically effective amount and concentration for preventing aestenosis. For example, 100 mcg/ml of Heparin may be used as disclosed in "Effect of Controlled Adventitial Heparin Delivery on Smooth Muscle Cell Proliferation" by Edelman et al., Proc. Natl. Acad. Sci. (USA) 1990; 87: 3773–3778, which is incorporated herein by reference. The drug is provided at a pressure ranging from a minimal value over zero to 50 pounds per square inch (depending on the volume and concentration of drug desired). Other pressures are contemplated for other uses as per the flexible nature of this device. The blood in the vessel continues to flow through the center of the flow lumen created through the center of the balloons and the sheath. Since the flow lumen created through the center of the balloons and sheath is relatively large (compared to the size of the blood vessel), the interruption of blood flow through the blood vessel is minimized. Further, since the blood flow is isolated from the containment pocket, the drug is only administered locally and does not enter the blood stream until the balloons are deflated. This allows for the drug to be provided to the vessel wall in high concentrations without providing a high concentration of the drug in the blood stream. After the drug has been applied to the vessel wall for the desired time, the device is removed. Because of the large volume of blood flow accommodated by this invention, numerous applications of the drug may be effected without removing the drug delivery device for a relatively long period of time.

Therefore, the present drug delivery catheter of the present invention may be used to more safely deliver agents intended to eliminate the occurrence of restenosis. Some exemplary agents for this purpose are heparin, calcium channel blockers, angiotensin converting enzyme inhibitors, fish oil, and growth peptides, thromboxane synthetase inhibitor, serotonin antagonists, HMGCoA reductase inhibitors, platelet derived growth factors, inflammatory cell factors, platelet aggregation inhibitors, and thrombin inhibitors such as hirudin or its analogs.

The catheter of the present invention may also be used to deliver agents which are intended to dissolve existing stenosis as an alternative to or in conjunction with other procedures such as angioplasty or atherectomy procedures. The agents delivered may dissolve thrombus at the lesion site. Suitable drug agents for the purpose am tissue plasminogen activator, streptokimose, and urokinase.

The foregoing description of the exemplary and preferred embodiments of the present invention has been presented for purposes of illustration and description. They are not intended to be exhaustive or to limit the invention to the precise forms disclosed, and obviously many modifications and variations are possible in light of the above teachings. The embodiments were chosen and described in order to best explain the principle of the invention and its practical applications and to thereby enable others skilled in the art to best utilize the invention in various embodiments and with various modifications as are suited to the particular use contemplated. It is intended that the scope of the invention be defined by the following claims, including all equivalents.

We claim:

1. A blood perfusion balloon catheter comprising:
   a) an elongate tubular shaft having a proximal portion and a distal portion;
   b) a plurality of toroidal-shaped inflatable balloons laced through the distal portion of the tubular shaft, the balloons creating a blood flow lumen when in the inflated state; and
   c) an inflation lumen in fluid communication with the inflatable balloons for inflating the inflatable balloons.

2. A blood perfusion balloon catheter for insertion into a vessel comprising:
   a) an elongate tubular member having a proximal end and a distal end;
   b) a toroidal-shaped inflatable balloon assembly laced through the distal end of the tubular member, the balloon assembly including a plurality of toroidal-shaped inflatable balloon members having an uninflated state and an inflated state;
   the balloon assembly configured such that 1) when the balloon member is in an uninflated state, the blood in the vessel may flow around the balloon assembly, and 2) when the balloon members are in an inflated state, a flow lumen is defined through the balloon members to allow the blood to flow through the balloon members; and
   c) an inflation lumen in fluid communication with the balloon members for inflating the balloon members.

3. The blood perfusion balloon catheter of claim 2 further comprising a guide wire lumen for receiving a guide wire.

4. The blood perfusion balloon catheter of claim 3 wherein the flow lumen is of a greater diameter than the guide wire lumen.

5. A blood perfusion catheter for insertion into a vessel comprising:
   a) an elongate tubular shaft having a distal end and a proximal end;
   b) a balloon assembly comprising a plurality of inflatable toroidal-shaped balloons laced through the distal end of the tubular shaft and a sheath attached to the toroidal shaped balloons, the balloon assembly configured such that when the toroidal shaped balloons are inflated, the sheath forms a flow lumen allowing for blood to flow through the inflated balloon assembly; and
   c) an inflation lumen in the tubular shaft in fluid communication with the toroidal-shaped balloons.

6. The blood perfusion catheter of claim 5 wherein the sheath is cylindrical.

7. The blood perfusion balloon catheter of claim 5 wherein the guide wire lumen runs substantially coaxially through the length of the tubular member.

8. The blood perfusion catheter of claim 5 wherein the sheath is attached to the torodial-shaped balloons at a section of the toroidal-shaped balloons that is radially inward of the outer diameter of the toroidal-shaped balloons.

9. A blood perfusion catheter for insertion into a vessel comprising:
   a) an elongate tubular member having a proximal end and a distal end;
   b) an inflatable balloon assembly disposed at the distal end of the tubular member, the balloon assembly including an inflatable balloon member having an uninflated state and an inflated state;
   the balloon assembly configured such that 1) when the balloon member is in an uninflated state, the blood in the vessel may flow around the balloon assembly, and 2) when the balloon member is in an inflated state, a flow lumen is defined through the balloon member to allow the blood to flow through the balloon member; and
   c) an inflation lumen in fluid communication with the balloon member for inflating the balloon member;
   the balloon assembly comprising a first toroidal balloon, a second toroidal balloon disposed distally of the first toroidal balloon, additional toroidal balloons disposed between the first and second toroidal balloons, and a cylindrical sheath connected between the first and second toroidal balloons, wherein the flow lumen is defined through the center of the cylindrical sheath and the first and second toroidal balloons are in fluid communication with each other.

10. The blood perfusion catheter of claim 9 wherein the diameter of the sheath is less than the diameter of the toroidal balloons.

* * * * *